United States Patent [19]

Durr et al.

[11] 4,132,797

[45] Jan. 2, 1979

[54] METHOD OF STIMULATING LEUKEMIC IMMUNE RESPONSE

[75] Inventors: Frederick E. Durr, Ridgewood; Martin R. Damiani, Allendale, both of N.J.

[73] Assignee: American Cyanamid Company, Stamford, Conn.

[21] Appl. No.: 807,780

[22] Filed: Jun. 20, 1977

[51] Int. Cl.² .................................................. A61K 31/425
[52] U.S. Cl. ................................................................ 424/270
[58] Field of Search ......................................... 424/270

[56] References Cited

U.S. PATENT DOCUMENTS

| 3,899,583 | 12/1975 | Spicer et al. ........................ 424/270 |
| 4,014,892 | 3/1977 | Spicer ................................ 424/270 |

Primary Examiner—Jerome D. Goldberg
Attorney, Agent, or Firm—Edward A. Conroy, Jr.

[57] ABSTRACT

Various acylaminotetramisoles have been shown to be effective leukemic immunostimulant agents.

7 Claims, No Drawings

METHOD OF STIMULATING LEUKEMIC IMMUNE RESPONSE

BACKGROUND OF THE INVENTION

The compounds of the present application have been elaborately set forth and described in Spicer et al., U.S. Pat. No. 3,899,587. In that instance, the alleged utility was for the treatment of helminthiasis in warm-blooded animals. These compounds are also the subject of Spicer et al. U.S. Pat. No. 4,014,892, in which usefulness for the control of whipworm is alleged.

SUMMARY OF THE INVENTION

This application discloses a method for stimulating the leukemic immune response in warm-blooded animals by orally administering to said animals a leukemic immunostimulating amount of a compound of the formula:

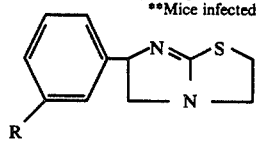

wherein R is selected from the group consisting of methoxycarbonylamino, m-chlorobenzoylamino, p-nitrobenzoylamino, chloroacetylamino and cyclohexylcarbonylamino and a pharmaceutically acceptable salt thereof.

DESCRIPTION OF THE PREFERRED EMBODIMENT

The compounds of the present invention are active as leukemic immunostimulants when tested according to the procedures set forth in the following references: "Humoral and Cellular Immune Responses in Susceptible and Resistant Strains of Mice Infected with Friend Leukemia Virus", W.S. Ceglowski, et al., Proc. Soc. Exp. Biol. & Med., 146, 619–624 (1974), and "Stimulation of Humoral and Cellular Antibody Formation in Mice by Poly IrCr", W. Turner, et al., Proc. Soc. Exp. Biol. & Med., 133, 334–338 (1970).

In particular, the following protocol was observed: Rauscher leukemia virus was inoculated intraperitoneally into BALB/C mice. The virus inoculum was a 20% (w/v) spleen extract made from 21-day infected spleens of BALB/C mice. All mice were within a 3 g. weight range with a minimum weight of 18 g. and all mice were male. Sheep red blood cells were injected intraperitoneally on the seventh day. There were 5 mice per test group. The test compound was administered orally on the sixth day as 0.5 ml. (in 0.2% Noble agar in saline) at a dose of 5 to 50 mg/kg of body weight and again on the seventh and eighth day in the same manner. On the fourteenth day the mice were weighed and bled from the retro-orbital sinus. The blood was pooled and the harvested serum stored at 4° C. for 24 hours. Hemagglutinin tests were performed by standard procedures using the microtiter plate technique. Acceptable hemagglutinin titer for leukemic (immunosuppressed) mice is $\leq$ 1:128. Positive control compounds were Poly IrCr (polyinosinic acid:polycytidylic acid) administered intraperitoneally on days +6 +7 and +8 and Tilorone given orally on days +6 +7 and +8. Acceptable positive control hemagglutinin titers are 4-fold higher than the titers obtained in the leukemic control mice.

The results of this test using the compounds of this invention appear in Table I.

TABLE I

Effect of Treatment on Antibody Response to Sheep Red Blood Cells in Leukemic Mice

| Compound | Dose mg/kg | Hemagglutinin Titer* | | | | |
|---|---|---|---|---|---|---|
| | | Test 1 | Test 2 | Test 3 | Test 4 | Test 5 |
| dl-m-(2,3,5,6-Tetrahydroimidazo[2,1-b)thiazol-6-yl)carbanilic acid methyl ester hydrochloride | 20 | | 128 | | | |
| | 10 | | 128 | | | |
| | 5 | | 256 | 256 | | |
| 3-Chloro-3'-(2,3,5,6-tetrahydroimidazo[2,1-b]-thiazol-6-yl)benzanilide | 5 | 128 | | 512 | | |
| 2-Chloro-3'-(2,3,5,6-tetrahydroimidazo[2,1-b]-thiazol-6-yl)acetanilide | 50 | | | | 512 | |
| | 5 | | | 256 | | |
| 4-Nitro-3'-(2,3,5,6-tetrahydroimidazo[2,1-bI]-thiazol-6-yl)benzanilide | 5 | | | 1024 | | 512 |
| 3'-(2,3,5,6-Tetrahydroimidazo[2,1-b]thiazol-6-yl)cyclohexanecarboxanilide | 10 | | | 256 | | |
| | 5 | | | 128 | | 512 |
| | 2.5 | | | 32 | | |
| Poly I:C | 10 | | 512 | 4096 | 1024 | |
| Tilorone | 200 | 512 | 256 | | 512 | 1024 |
| Non-infected, immunized (sheep red blood cells) controls | | 4096 | 1024 | 4096 | 2048 | 4096 |
| Infected, immunized controls** | | 32 | 64 | 64 | 128 | 128 |

*Reciprocal of serum dilution producing at least 50% agglutination of sheep red blood cells.
**Mice infected 7 days prior to injection of sheep red blood cells with Rauscher leukemia virus.

The compounds of the present invention are active orally as leukemic immunostimulants. A range of doses may be employed depending on the mode of administration. For oral administration these compounds are usually administered at from about 5 to about 50 mg/kg/day.

In therapeutic use, the compounds of this invention may be administered in the form of conventional pharmaceutical compositions. Such compositions may be formulated so as to be suitable for oral administration. The active ingredient may be combined in admixture with a pharmaceutically acceptable carrier, which carrier may take a wide variety of forms depending on the form of preparation desired for administration. These compounds can be used in compositions such as tablets. Here, the prinicpal active ingredient is mixed with conventional tabletting ingredients such as corn starch, lactose, sucrose, sorbitol, talc, stearic acid, magnesium stearate, dicalcium phosphate, gums or similar materials as non-toxic, pharmaceutically acceptable diluents or carriers. The tablets or pills of these novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye.

The liquid forms in which the novel compositions of the present invention may be incorporated for administration include suitable flavored suspensions, elixirs, emulsions, solutions and similar pharmaceutical vehicles.

These dosage forms refer to physically discrete units suitable as unitary dosage for warm-blooded animals, each unit containing a predetermined quantity of active component calculated to produce the desired therapeutic effect in association with the required pharmaceutical diluent, carrier or vehicle. The specification for the novel dosage forms of this invention are indicated by characteristics of the active component. Examples of suitable dosage forms are tablets, capsules, pills, powder packets, granules, wafers, cachets, teaspoonfuls, dropperfuls, segregated multiples of any of the foregoing and other forms as herein described.

We claim:

1. A method for stimulating the leukemic immune response in a warm-blooded animal in need of said stimulation which comprises orally administering to said animal an effective leukemic immunostimulating amount of a racemic mixture or levorotatory isomer of a compound selected from the group consisting of those of the formula:

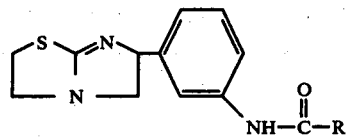

wherein R is methoxy, chloromethyl, cyclohexyl, m-chlorophenyl or p-nitrophenyl and the pharmaceutically acceptable acid-addition salts thereof.

2. The method according to claim 1 wherein R is methoxy and the compound is the racemic mixture as the hydrochloric acid salt; dl-m-(2,3,5,6-tetrahydroimidazo[2,1-b]thiazol-6-yl)carbanilic acid methyl ester hydrochloride.

3. The method according to claim 1 wherein R is methoxy and the compound is the levorotatory isomer as the hydrochloric acid salt; 1-m-(2,3,5,6-tetrahydroimidazo[2,1-b]thizol-6-yl)carbanilic acid methyl ester hydrochloride.

4. The method according to claim 1 wherein R is m-chlorophenyl and the compound is the racemic mixture in the free base form; dl-3-chloro-3'-(2,3,5,6-tetrahydroimidazo[2,1-b]thiazol-6-yl)benzanilide.

5. The method according to claim 1 wherein R is chloromethyl and the compound is the racemic mixture in the free base form; dl-2-chloro-3'-(2,3,5,6-tetrahydroimidazo[2,1-b]thiazol-6-yl)acetanilide.

6. The method according to claim 1 wherein R is p-nitrophenyl and the compound is the racemic mixture in the free base form; dl-4-nitro-3'-(2,3,5,6-tetrahydroimidazo[2,1-b]thiazol-6-yl)benzanilide.

7. The method according to claim 1 wherein R is cyclohexyl and the compound is the racemic mixture in the free base form; dl-3'-(2,3,5,6-tetrahydroimidazo[2,1-b]-thiazol-6-yl)cyclohexanecarboxanilide.

* * * * *